US006784204B2

(12) United States Patent
He et al.

(10) Patent No.: US 6,784,204 B2
(45) Date of Patent: Aug. 31, 2004

(54) ANTIBIOTIC CYTOSPORACIN

(75) Inventors: Haiyin He, Washington Township, NJ (US); Jeffrey Edwin Janso, Montclair, NJ (US)

(73) Assignee: Wyeth Holdings Corporation, Five Giralda Farms, Madison, NJ (US)

( * ) Notice: Subject to any disclaimer, the term of this patent is extended or adjusted under 35 U.S.C. 154(b) by 0 days.

(21) Appl. No.: 10/684,546

(22) Filed: Oct. 14, 2003

(65) Prior Publication Data

US 2004/0082648 A1 Apr. 29, 2004

Related U.S. Application Data

(60) Provisional application No. 60/418,605, filed on Oct. 15, 2002.

(51) Int. Cl.[7] .................. C12P 17/16; A61K 31/365; C07N 311/74
(52) U.S. Cl. .................. 514/455; 435/118; 549/280
(58) Field of Search .................. 549/280; 514/455; 435/118

(56) References Cited

PUBLICATIONS

He et al, Journal of Organic Chemistry, vol. 68, No. 16, p.6079–6082 (2003).*
Crawley, Graham C.; J. Chem. Soc., Perkin Trans. 1 (1), pp. 221–223 (1981).
Boulet, Camille A., et al.; Can. J. Chem., 61 (10), pp. 2285–2286, (1983).
"Nosocornial Enterococci Resistant to Vancomycin", Morbidity and Mortality Weekly Report 42, (30), pp. 597–598, (1993).
Handwerger, et al., Clin. Infect. Dis. (16), pp. 750–755, (1993).

* cited by examiner

Primary Examiner—Bernard Dentz
(74) Attorney, Agent, or Firm—Daniel B. Moran

(57) ABSTRACT

This disclosure describes new antibiotic Cytosporacin having the structure:

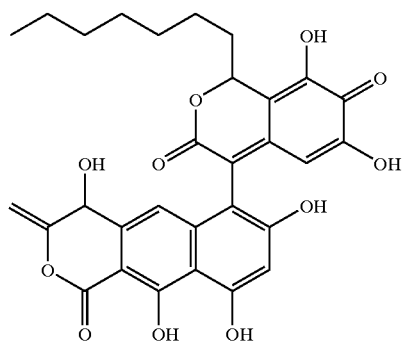

The invention relates to a new antibiotic designated Cytosporacin, to its production by fermentation, to methods for its recovery and concentration from the crude solutions, and to process for its purification. The invention includes within its scope the agent in dilute form, as a crude concentrate, and in pure form. The invention also relates to the use of the compound according to the invention in antimicrobial compositions and as antiseptics or disinfectants.

7 Claims, 3 Drawing Sheets

ULTRA VIOLET ABSORPTION SPECTRUM OF CYTOSPORACIN (1:1 ACETONITRILE/WATER).

ANTIBIOTIC CYTOSPORACIN

This application claims priority from copending provisional application, Application No. 60/418,605 filed Oct. 15, 2002 the entire disclosure of which is hereby incorporated by reference.

FIELD OF THE INVENTION

The invention relates to a new antibiotic designated Cytosporacin, to its production by fermentation, to methods for its recovery and concentration from the crude solutions, and to process for its purification.

BACKGROUND OF THE INVENTION

New improved antibiotics are continually in demand, for the treatment of diseases in man. Antibiotic resistant organisms are continually a problem, with Vancomycin the last defense, particularly in hospitals. Especially in hospitals, isolates which are vancomycin resistant are becoming more common. A recent survey found 7.9% of Enterococci in United States hospitals are now vancomycin resistant. "Nosocomial Enterococci Resistant to Vancomycin" Morbidity and Mortality Weekly Report 42(30):597–599(1993). Further resistance of Vancomycin and other antibiotics to *Enterococcus faecium* is reported, Handwergers. et al., Clin. Infect. Dis. 1993(16),750–755. Resistance organisms are also a problem for other important antibiotics which includes piperacillin.

Clearly, antibiotic resistance is a growing public health problem and having new antibiotics available could provide additional options for physicians in treatment regimens.

The medical community recognizes that there is an ongoing need for additional antibiotics. The search for new antibiotics which exhibit antibacterial activity against vancomycin-resistant isolates and having structures which are not derivatives of vancomycin are particularly appealing.

Antibiotics described in the literature include: Crawley, Graham C. Isolation of three new isochroman-3-one metabolites from *Oidiodendron rhodogenum* Robak. *J. Chem. Soc., Perkin Trans.*1 (1981), (1), 221–3 and Boulet, Camille A.; Poulton, Gerald A. Pentaketide metabolites from *Potebniamyces gallicola* n. sp. *Can. J. Chem.* (1983), 61(10), 2285–6.

However, all of the above disclosed antibiotics are distinct from the present invention.

SUMMARY OF THE INVENTION

The present invention relates to an antibiotic compound having the structure:

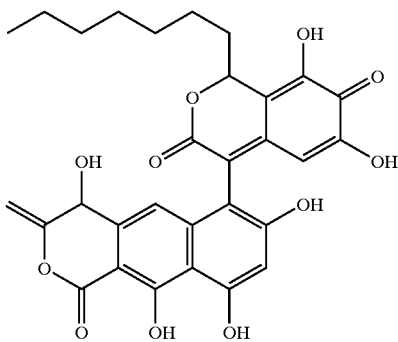

The present invention includes within its scope the agent in dilute form, as a crude concentrate, and in pure form. The present invention also relates to the use of the compound according to the invention in antimicrobial compositions and as an antiseptic, or disinfectant.

It is an object of this invention to provide Cytosporacin, an antibiotic which is shown to possess antibacterial activity, especially against vancomycin resistant bacterial isolates and in particular having a chemical structure unlike vancomycin.

DESCRIPTION OF THE PREFERRED EMBODIMENTS

The invention relates to new antibiotic Cytosporacin, to the production of the antibiotic by fermentation, to methods for the recovery and concentration of the antibiotic from crude solutions, and to processes for the purification of the antibiotic. The invention includes within its scope the new antibiotic in diluted form, as crude concentrate and in pure form. The novel antibiotic is useful as an antibacterial agent.

The new antibiotic designated Cytosporacin is formed during the fermentation of *Cytospora rhizophorae* ATCC38475.

The structure of the new antibiotic Cytosporacin is:

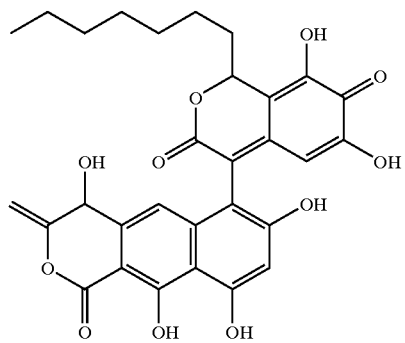

Figure 1:
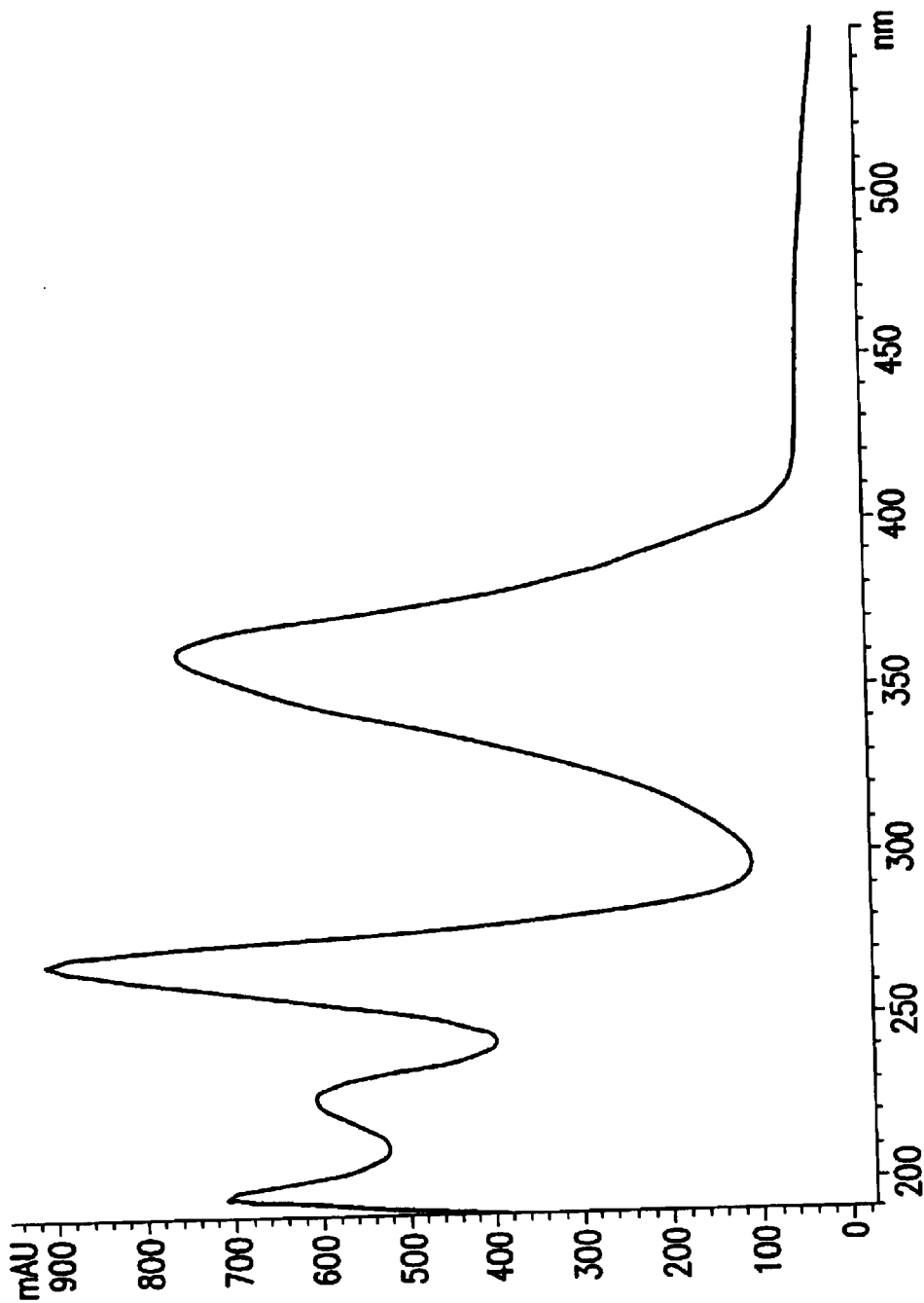
FIG. 1. Ultra violet absorption spectrum of Cytosporacin.
Figure 2:
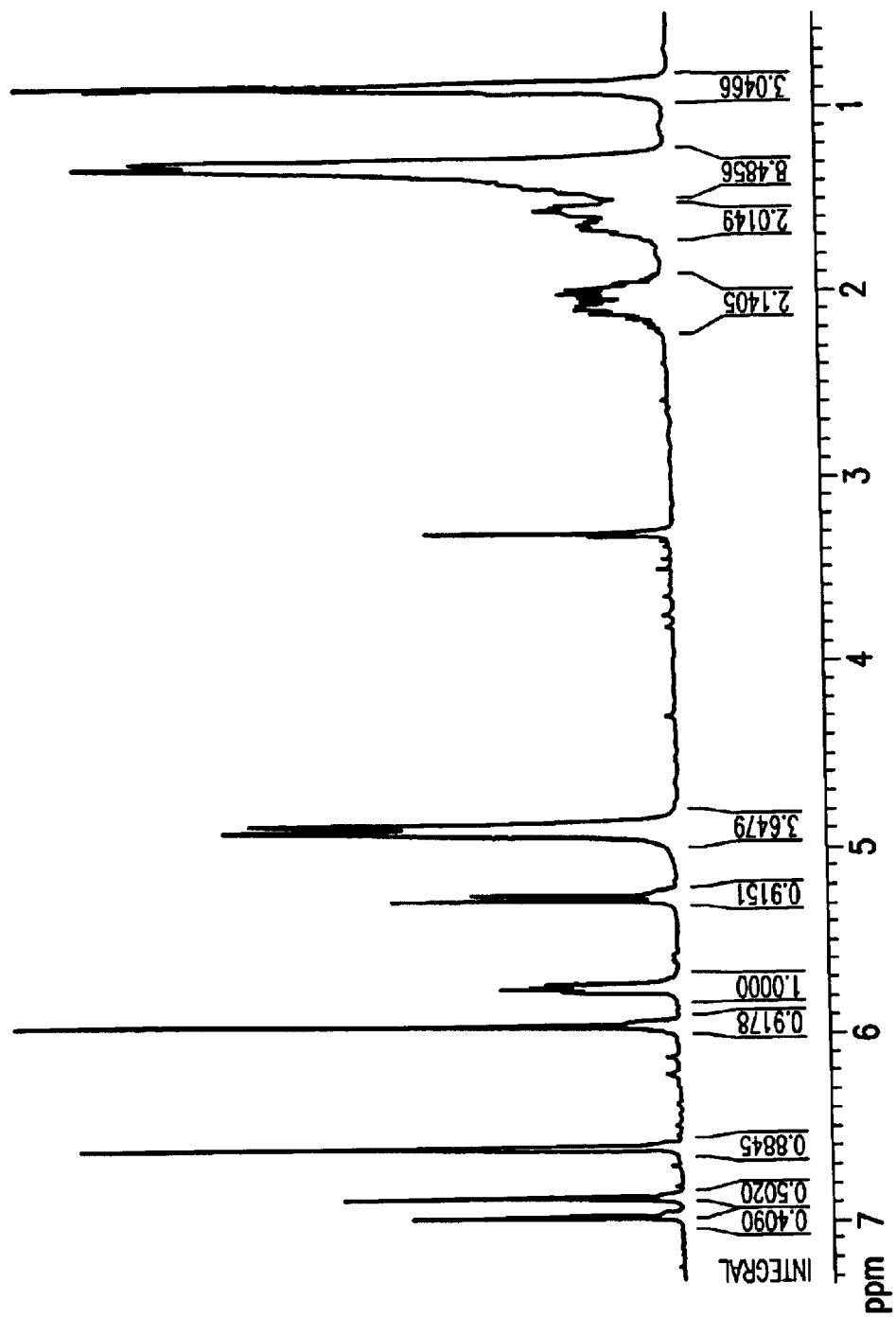
FIG. 2. Proton nuclear magnetic resonance spectrum of Cytosporacin in $CD_3OD$ at 300 MHz.
Figure 3:
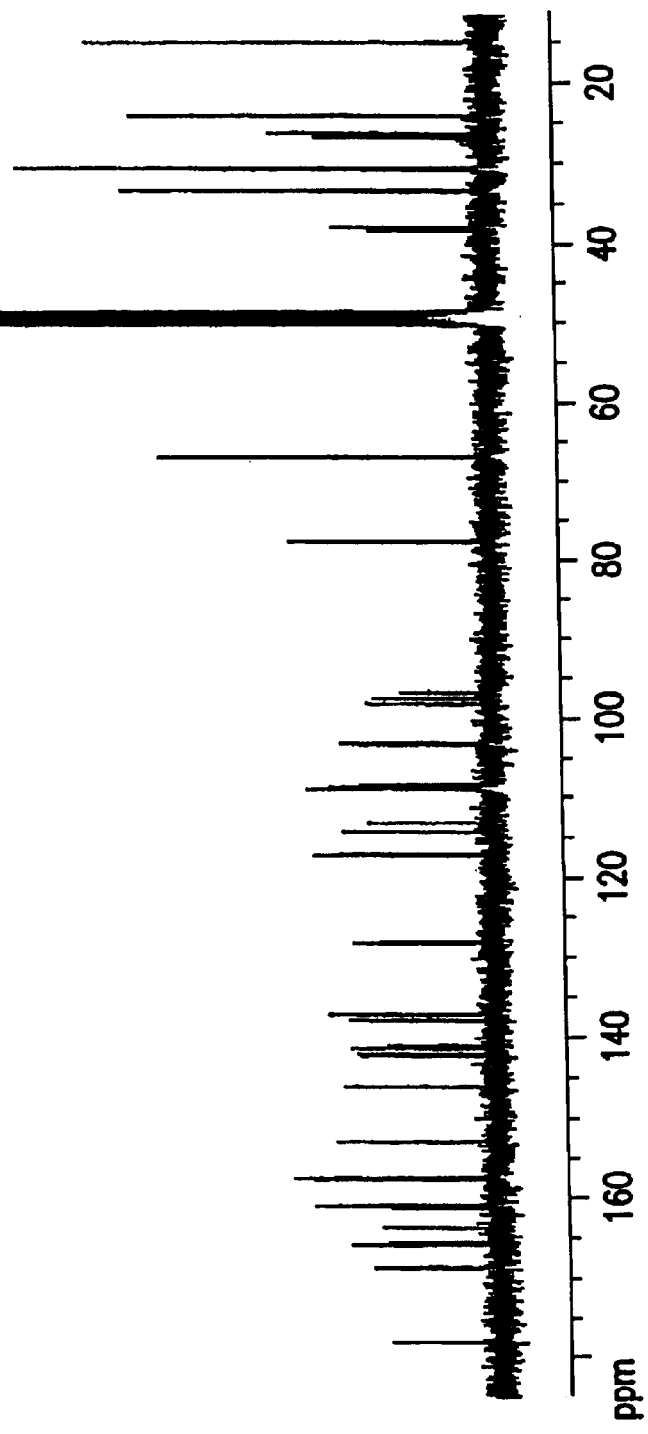
FIG. 3. Carbon-13 nuclear magnetic resonance spectrum of Cytosporacin in $CD_3OD$ at 75 MHz.

The physico-chemical characteristics of Cytosporacin are as follows:

1. Molecular weight: 564;
2. Apparent molecular formula: $C_{30}H_{28}O_{11}$;
3. Ultra violet absorption spectrum as shown in FIG. 1 (1:1 acetonitrile/water);
4. Proton nuclear magnetic resonance spectrum as shown in FIG. 2 (300 MHz, $CD_3OD$);
5. Carbon-13 nuclear magnetic resonance spectrum as shown in FIG. 3 (75 MHz, $CD_3OD$), with significant signals listed:

| | | | | | | |
|---|---|---|---|---|---|---|
| 177.77 | 177.72 | 168.34 | 168.28 | 165.56 | 165.14 | 163.38 |
| 163.34 | 160.94 | 160.71 | 160.56 | 160.57 | 152.67 | 152.59 |
| 145.84 | 145.80 | 142.04 | 141.80 | 141.16 | 140.80 | 137.50 |
| 127.95 | 127.78 | 116.89 | 114.05 | 112.81 | 108.61 | 108.53 |
| 108.47 | 108.35 | 108.07 | 103.06 | 102.87 | 97.93 | 97.89 |
| 97.24 | 96.53 | 77.37 | 77.39 | 66.48 | 38.06 | 37.59 |

-continued

| | | | | | | |
|---|---|---|---|---|---|---|
| 33.01 | 32.90 | 30.35 | 30.21 | 30.20 | 26.27 | 25.83 |
| 23.69 | 23.65 | 14.50 | 14.46 | | | |

The new antibacterial agent Cytosporacin is formed during the cultivation under controlled conditions of fungus *Cytospora rhizophorae* ATCC38475.

ATCC38475 grows well on potato dextrose agar (Difco). After 7 days growth at 22° C. colonies are felty to lightly floccose to fuzzy and some mycelia are submerged. The margin is lobate to irregular. The surface color is buff to cream and the reverse is yellowish to tan to white. After longer incubation pycnidia formation occurs. They are less than 1 millimeter in diameter and ooze a yellow spore mass.

For the production of the new antibiotic, the present invention is not limited to this particular organism or to organisms fully answering the above characteristics, which are given for illustration purpose only. It is desired and intended to include the use of mutants produced from this organism by various means such as exposures to X-radiation, ultraviolet radiation, N'-methyl-N'-nitro-N-nitrosoguanidine, phages, and like.

STANDARD PHARMACOLOGICAL TEST PROCEDURES

Biological Activity

The minimum inhibitory concentration (MIC), the lowest concentration of the antibiotic which inhibits growth of the test organism, is determined by the broth dilution method using Muller-Hinton II agar (Baltimore Biological Laboratories) following the recommendations of the National Committee for Clinical Laboratory Standards [Methods for dilution antimicrobial susceptibility tests for bacteria that grow aerobically. Approved standard M7-A2. National Committee for Clinical Laboratory Standards, Villanova, Pa].

An inoculum level of 5×10$^5$ CFU/ml, and a range of antibiotic concentrations (256–1.0 µg/ml) is used. The MIC is determined after the microtiter plates are incubated for 18 hours at 35° C. in an ambient air incubator. The test organisms comprise a spectrum of Gram-positive bacteria comprised of Staphylococcus sp., Enterococcus sp., Gram-negative bacterium *Escherichia coli*, and the yeast *Candida albicans*. These organisms include recent clinical isolates that are resistant to piperacillin and vancomycin. MIC data of Cytosporacin are listed in Table 1.

TABLE 1

MIC of Cytosporacin.

| Organism | MIC (µg/ml) |
|---|---|
| *Staphylococcus aureus* 375 (ATCC3538p) | 32 |
| *Staphylococcus aureus* 310 (SSC8224, methicillin-resistant) | 32 |
| *Enterococcus faecium* 379 (NC12204, vancomycin-resistant) | 64 |
| *Enterococcus faecium* 436 (ID3151) | 16 |
| *Bacillus subtilis* 327 (BGSC-1A1) | 32 |
| *Escherichia coli* 389 (GC4560 imp) | 64 |
| *Escherichia coli* 442 (GC4559) | 256 |
| *Candida albicans* 54 (CA300) | >256 |

The in vitro antimicrobial results show that the product according to the invention has activity against Gram-positive bacteria tested.

Antibiotic Cytosporacin derives its utility from antibacterial activity. For example, Cytosporacin may be used in the suppression of bacterial infections, as a topical antibacterial agent or as a general disinfectant. Cytosporacin is not limited to the uses listed. In therapeutic use, the compound of this invention may be administered in the form of conventional pharmaceutical compositions appropriate for the intended use. Such compositions may be formulated as to be suitable for oral, parenteral or topical administration. The active ingredient may be combined in admixture with a nontoxic pharmaceutical carrier that may take a variety of forms depending on the form of preparation desired for administration, i.e. oral, parenteral, or topical.

When the compounds are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight. An effective amount of compound from 0.01 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition of the host undergoing therapy. Additionally, the antibacterially effective amount of the antibiotic of the invention may be administered at a dosage and frequency without inducing side effects commonly experienced with conventional antibiotic therapy which could include hypersensitivity, neuromuscular blockade, vertigo, photosensitivity, discoloration of teeth, hematologic changes, gastrointestinal disturbances, ototoxicity, and renal, hepatic, or cardiac impairment. Further the frequency and duration of dosage may be monitored to substantially limit harmful effects to normal tissues caused by administration at or above the antibacterially effective amount of the antibiotic of the invention.

The active compound of the invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA. The active compound may also be administered parenterally or intraperitoneally. Solutions or suspensions of the active compound as a free base or pharmacologically acceptable salt can be prepared in glycerol, liquid, polyethylene glycols and mixtures thereof in oils. Under ordinary conditions of storage and use, these preparations contain a preservative. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention accordingly provides a pharmaceutical composition which comprises a compound of this invention in combination or association with a pharmaceutically acceptable carrier. In particular, the present invention provides a pharmaceutical composition which comprises an antibacterially effective amount of a compound of this invention and a pharmaceutically acceptable carrier.

The present invention further provides a method of treating bacterial infections in warm-blooded animals including man, which comprises administering to the afflicted warm-blooded animals an antibacterially effective amount of a compound or a pharmaceutical composition of a compound of the invention. The invention will be more fully described in conjunction with the following specific examples which are not to be construed as limiting the scope of the invention.

As used herein an effective amount refers to the quantity of a compound of the invention which is sufficient to yield a desired therapeutic response without undue adverse side effects (such as toxicity) commensurate with a reasonable benefit/risk ratio when used in the method of this invention.

Further, antibiotic Cytosporacin can be used in antimicrobial compositions, especially as an antiseptic by local and general application, and as a disinfectant.

The Cytosporacin according to the invention, which has good antimicrobial activity may be used in antimicrobial compositions, especially as an antiseptic by local and general application, and as a disinfectant.

As antiseptics for human or veterinary use, the concentration of active product can vary from about 0.01% to 5% by weight according to the use and the chosen formulation. Thus, it is possible to prepare foaming detergent solutions to be used by surgeons and nursing staff for washing their hands or to be used for cleansing dermatological lesions such as impetigo, pityriasis and leg ulcers. Foaming detergent solutions are also used as shampoos (for example antidandruff shampoos) or for the preparation of shower gels, shaving creams and foaming lotions. Foaming solutions containing Cytosporacin according to the invention are obtained using amphoteric, anionic, cationic or non-ionic surfactants at a concentration of about 0.3 to 30%, humectants such as glycols or polyethylene glycols, at a concentration of 0 to 20% ethylene oxide and polypropylene copolymers at a concentration of 0 to 20%, and an alcohol (ethanol, isopropanol, benzyl alcohol) or a polyol, such as glycerol, at a concentration of 0 to 15%, as well as agents for complexing Ca++, Mg++ and heavy metal ions, salts for providing an appropriate buffer capacity, agents for imparting viscosity, such as NaCl or KCl, natural, cellulosic or synthetic polymers such as polyvinylpyrrolidone, thickening superfatting agents such as polyethylene glycol distearate or copra monoethanolamide or diethanolamide, fragrances, preservatives and colorants.

It is possible to use microemulsions, micellar solutions or any other phase of the ternary or quaternary diagram of water/active principle/surfactant/co-surfactant which permits solubilization of Cytosporacin in water. These solutions can be used in diluted or undiluted form and can be dispensed for example by means of a vasopump or liquefied or non-liquefied propellants.

With the same constituents at appropriate concentrations, the product according to the invention can also be used to prepare simple aqueous solutions or aqueous solutions in the form of sprays for making operative fields antiseptic, for postoperative treatments, for the treatment of burns, superinfected eczema, gluteal erythema, wounds or acne, or for deodorants.

Simple alcoholic solutions or alcoholic solutions in the form of sprays containing 20 to 80% by weight of alcohol can contain, apart from the excipients used in aqueous solutions, excipients which make it possible to penetrate the keratinized layers of the skin and superficial body growths, such as Azone (marketed by Nelson Research) and Transcutol (marketed by Gattefosse). These solutions are to be used for making the skin antiseptic before puncture, for preparing the operative field, by nursing staff for making their hands antiseptic and for treating closed infected dermatosis, folliculitis, perionychia or acne.

Cytosporacin according to the invention can be applied in the form of creams together with the fatty substances normally found in the preparation of creams or emulsions.

Cytosporacin according to the invention can also be used in animals for indications such as the prevention or treatment of infected lesions. In this case, the pharmaceutical compositions are similar to those used in man, in particular creams sprays or solutions.

Moreover, the rapid lethal action on germs of Cytosporacin according to the invention may be used as surface disinfectants at concentrations which can vary from about 0.1 to 4% by weight. In this case, Cytosporacin is used in preparations such as aqueous or non-aqueous foaming detergent solutions, sprays or nebulizers. This type of preparation is particularly useful in the hospital or veterinary sectors. These preparations can contain the same constituents as those used in the antiseptic formulations, although a variety of organic solvents may be added.

GENERAL FERMENTATION CONDITION

Cultivation of ATCC38475 may be carried out in a wide variety of liquid culture media. Media which are useful for the production of Cytosporacin include an assimilable source of carbon, such as dextrin, sucrose, molasses, glycerol, etc.; an assimilable source of nitrogen, such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicon oil may be added as needed.

A culture of ATCC38475 is inoculated into potato dextrose broth and incubated at 22° C. with aeration.

GENERAL ISOLATION PROCEDURE OF CYTOSPORACIN

The Cytosporacin is recovered from the fermentation broth by extracting cells with methanol and supernatant with 1-butanol. The combined extract is evaporated under reduced pressure and the concentrate purified by HPLC on a C18 column using acidic acetonitrile in water to afford Cytosporacin as an amorphous red powder.

The invention is further described in conjunction with the following non-limited examples.

EXAMPLE 1

Inoculum Preparation

ATCC38475 is plated into Bennett's agar medium (10 g/l Sigma D-glucose, 1 g/l Difco beef extract, 1 g/l Difco yeast extract, 2 g/l N-Z amine A, 20 g/l Difco agar) from a Difco potato dextrose agar slant and incubated at 22° C. Mycelia are scraped from the agar plate and inoculated into five 25×150 mm glass tubes containing two glass beads and 11 ml of potato dextrose broth. This liquid seed culture is shaken at 160 rpm at 22° C. for four days and then used to inoculate the production medium.

EXAMPLE 2

Fermentation

The production medium is one liter of potato dextrose broth in a 2.8 liter Fernbach flask. It is inoculated with the five tubes of seed culture and incubated at 200 rpm and 22° C. for 12 days.

EXAMPLE 3

Isolation and Purification of Cytosporacin

The whole broth (1 L) is centrifuged at 3800 rpm for 30 minutes. The supernatant and the cells are respectively extracted by 1-butanol (2×0.5 L) and methanol (2×0.5 L). The combined extract is evaporated under reduced pressure to dryness. The residue thus obtained is redissolved in a small volume of methanol, and is separated by high performance liquid chromatography (HPLC) on a C18 column (YMC ODS-A, 5 μm particle size, 70×500 mm in size) using a gradient solvent from 40 to 100% acetonitrile in water (35 minutes) and acetonitrile (10 minutes), with both solvents containing 0.01% in volume of trifluoroacetic acid. The UV peak with a retention time of 36 minutes, monitored at 360 nm, is collected. Upon evaporation, the red powder is redissolved in a small volume of methanol and purified by HPLC (C18 column (YMC ODS-A, 5 μm particle size, 70×500 mm in size) using a gradient solvent from 40 to 100% acetonitrile in water and acetonitrile) to afford the pure Cytosporacin.

What is claimed is:

1. The compound which has the structure:

2. A method of treating a warm-blooded animal affected by bacterial infections, which method comprises administering to said warm-blooded animal an effective amount of a compound of claim 1.

3. A pharmaceutical composition comprising an effective amount of a compound of claim 1 together with a pharmaceutically acceptable carrier.

4. A process for the preparation of Cytosporacin which comprises cultivating *Cytospora rhizophorae* designated ATCC38475 or a mutant thereof under aerobic conditions, in a sterile liquid medium containing assimilable sources of carbon, nitrogen and inorganic anion and cation salts, until substantial antibiotic activity is imparted to said medium by the production of Cytosporacin, recovering and isolating antibiotic Cytosporacin.

5. A pharmaceutical or disinfectant composition which contains an effective antimicrobial, antiseptic or disinfectant amount of Cytosporacin of claim 1 as an active ingredient.

6. A pharmaceutical composition having antimicrobial, antiseptic and disinfectant activity as claimed in claim 5, wherein said effective amount of said antimicrobial compound Cytosporacin is from 0.01 to 5% by weight.

7. A disinfectant composition for inert surfaces as claimed in claim 5 wherein said effective amount of said antimicrobial compound Cytosporacin is from 0.1 to 4% by weight.

* * * * *